United States Patent [19]

Aguilar M.

[11] 4,267,831
[45] May 19, 1981

[54] NASAL AIR FILTER AND MEDICAMENT DISPENSER DEVICE

[76] Inventor: Rogelio M. Aquilar, P.O. Box 46, Alajuela, Costa Rica

[21] Appl. No.: 78,004

[22] Filed: Sep. 24, 1979

[51] Int. Cl.³ ............................................. A61M 15/08
[52] U.S. Cl. .......................... 128/203.14; 128/203.22; 128/206.11
[58] Field of Search ....................... 128/206.11, 203.22, 128/203.14

[56] References Cited

U.S. PATENT DOCUMENTS

| | | | |
|---|---|---|---|
| 2,087,042 | 7/1937 | Phillips | 128/206.11 X |
| 2,097,846 | 11/1937 | Strauch | 128/206.11 X |
| 2,237,954 | 4/1941 | Wilson | 128/206.11 X |
| 2,264,153 | 11/1941 | Rowe | 128/206.11 X |
| 2,335,936 | 12/1943 | Hanlon | 128/206.11 X |
| 2,433,565 | 12/1947 | Korman | 128/206.11 X |
| 2,535,155 | 12/1950 | Pandorf | 128/206.11 X |
| 2,890,695 | 6/1959 | Safstrom | 128/206.11 X |
| 3,463,149 | 8/1969 | Albu | 128/206.11 X |
| 3,722,509 | 3/1973 | Nebel | 128/206.11 X |
| 3,905,335 | 9/1975 | Kapp | 128/206.11 X |
| 4,030,491 | 6/1977 | Mattila | 128/206.11 X |
| 4,052,983 | 10/1977 | Bovender | 128/206.11 X |

*Primary Examiner*—Henry J. Recla
*Attorney, Agent, or Firm*—Lowe, King, Price & Becker

[57] ABSTRACT

An intranasal device for filtering nasal air and dispensing medication to be inhaled comprises a pair of approximately cylindrical resilient containers joined together by a bridging member. The containers are adapted to be positioned within the nasal passages with the bridging member extending across the septum. The lower end of each container is formed of a filter material and a washer shaped plug saturated with a medicament is located within each container downstream of the filter. The washer shaped absorptive plug is conveniently inserted into and removed from each container through an access opening formed in the sidewall of the container. The plug is retained within each container at the end by a pair of cross members which permit axial flow-through of air. The device may be provided with at least one temperature sensor or other measurement probe to monitor characteristics of air flow within the nasal passages. The device may further be provided with at least one nozzle to dispense an antibiotic or other substance in addition to the medicament into the nasal air flow.

8 Claims, 7 Drawing Figures

U.S. Patent      May 19, 1981      4,267,831

NASAL AIR FILTER AND MEDICAMENT DISPENSER DEVICE

TECHNICAL FIELD

The present invention relates generally to devices for filtering and medicating air passing through the nasal passages, and more particularly, toward such a device including a medicated washer that is inserted and removed transversely through a sidewall of the device.

BACKGROUND ART

Many different types of intranasal filters and medicament inhalers have been provided in the prior art. Generally, these units are approximately cylindrical in shape and are adapted to be located within the nasal passages, connected together by a bridging member that extends across the septum. Each cylindrical member contains a quantity of filter material through which nasal air passes during breathing. In units containing a medicament unit, the nasal air passes through the medicament which is slowly dispensed into the air by evaporation or sublimation.

U.S. Pat. No. 3,905,335 to Kapp, for example, discloses a prior art nasal air filter over which the present invention is an improvement. The patented filter comprises a pair of cylindrical containers adapted to be inserted within the nasal passages. A quantity of filter material is retained within each cylinder by a pair of flanged end caps that are permanently formed to the cylinder. There is no provision for replacing the filter material, however, or for providing a medicament within the cylinder.

U.S. Pat. No. 4,030,491 to Mattila discloses a relatively complex nasal filter wherein filter material or medicament can be loaded or replaced through cover plates that are removeable from the lower end of each of a pair of filter containers. The covers are removed from the corresponding filter containers by sliding the covers along a bridging member interconnecting the containers.

Other U.S. Patents disclosing intranasal filter and medicament dispenser devices considered to be illustrative of the background art are Phillips No. 2,087,042, Wilson No. 2,237,954, Hanlon No. 2,335,936, Korman No. 2,433,565, Safstrom No. 2,890,695, Nebel No. 3,722,509, and Bovender No. 4,052,983.

A deficiency of the prior art nasal air filter and medicament units has been that none provide convenient initial application or replacement of the medicament, as exemplified by the relatively complex structure of the Mattila patent, supra. Furthermore, in devices containing a filter as well as a medicament dispenser, resistance to air flow by the filter and medicament has been excessive, causing difficulty in breathing. There exists a need, therefore, for a nasal filter and medicament unit that provides both low resistance to air flow and simplified removal and replacement of medication.

A primary object of the present invention, therefore, is to provide a new and improved nasal air filter and medicament dispenser device that provides simplified replacement of the medicament unit and offers reduced resistance to air flow.

Another object is to provide such a device that is worn comfortably within the nasal passages and is economical to produce.

In some types of diagnostics, it is necessary to measure a parameter, such as the temperature or bacteriological content of air passing through the nasal passages. Occasionally, a therapeutic substance such as an antibiotic must be dispensed at controlled intervals directly into the passage.

Another object of the present invention, therefore, is to provide an intranasal device capable of unobtrusively monitoring a parameter of air passing through the nostrils.

Still another object is to provide an unobtrusive intranasal device for injecting at controlled intervals a fluid substance directly into the nostrils.

DISCLOSURE OF INVENTION

A nasal air filter and medicament dispenser device, in accordance with the invention, comprises a pair of resilient, elliptic cylindrical containers adapted to be comfortably located within the nasal passages and connected together by a bridging member extending across the septum. A washer shaped, absorptive plug, saturated with a medicament, or solid medicated plug, is inserted into each container through an access opening formed in the sidewall of the container. The plug is retained in position within each container by friction between the rim of the plug and inner wall surface of the container and abuts a pair of mutually orthogonal cross members at the upper end of the container. The lower end of each container is formed of an elliptical filter which cleans the air entering the nasal passages prior to contact with the medicament as the air passes through the central aperture formed in the washer shaped plug.

A pair of parameter monitoring probes are located within each container adjacent the cross members to respond to air in the nasal passages. The probes are downstream of the filter and medicament to be exposed to air which is actually entering the body. A pair of dispensing nozzles are positioned adjacent the probes within each container to dispense a therapeutic fluid into the nasal air flow. The output of the nozzles may be controlled in response to signals generated by the probes.

Still other objects and advantages of the present invention will become readily apparent to those skilled in this art from the following detailed description, wherein I have shown and described only the preferred embodiment of the invention, simply by way of illustration of the best mode contemplated by me of carrying out my invention. As will be realized, the invention is capable of other and different embodiments, and its several details are capable of modifications in various obvious respects, all without departing from the invention. Accordingly, the drawings and description are to be regarded as illustrative in nature, and not as restrictive.

BEST MODE FOR CARRYING OUT THE INVENTION

Figure 1:
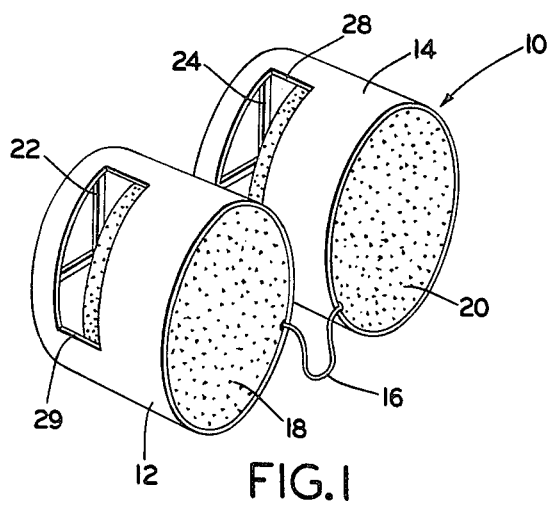
FIG. 1 is a perspective view of the nasal air filter and medicament dispensing device with medicated plugs removed.
Figure 4:
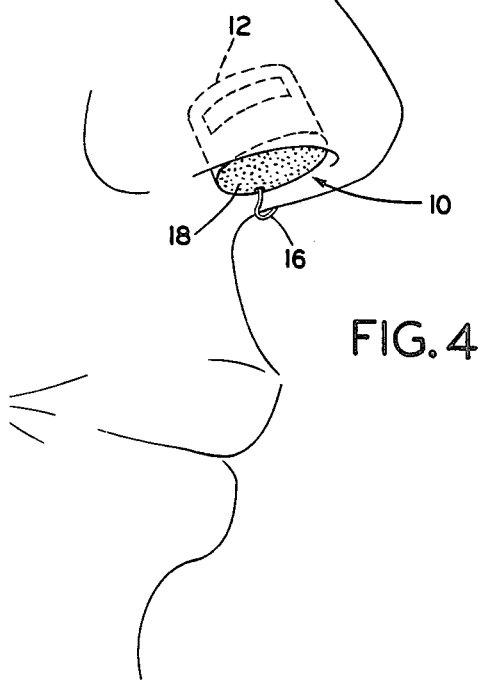
FIG. 4 is a view of the device as it is worn by the user.

Referring to FIG. 1, a nasal air filter and medicament dispensing device, identified generally by the numeral 10, comprises first and second resilient containers 12 and 14 that are preferably approximately cylindrical and slightly oblong in the form of elliptic cylinders, as shown, to seat comfortably within the nasal passages. The two containers 12 and 14 are formed of a relatively soft, pliable material, such as paper or a plastic and are joined together at one end by a cross member 16 adapted to bridge across the septum (see FIG. 4).

The lower end of each of the containers 12 and 14 contains an elliptical end unit 18, 20 formed of a filter material. The filter material is preferably attached to the container 12 by wrapping the container, in sheet form, around the filter using the filter as a mandril. The ends of the sheet are then bonded together to form a closed surface by a suitable adhesive and one end of the sheet is bonded to the filter to form the elliptic cylinder configuration.

Figure 2:
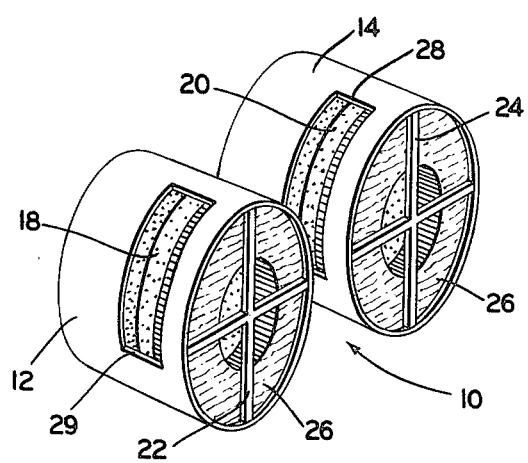
FIG. 2 is a perspective view of the device of FIG. 1 with the medicated plugs inserted.

At the opposite end of containers 12 and 14, a pair of cross pieces 22 and 24 form a screen or lattice for retaining a medicated pad or plug 26 (FIG. 3) within each container. The sidewall of each of the containers 12 and 14 has an access opening 25, 28 formed therein corresponding in size to the plug 26. The purpose of the access openings 25 and 28 is to enable insertion and removal of the plug 26 through the sidewall of the container without removing the filter ends 18 and 20. Plug 26 is shown inserted within the containers 12 and 14 in FIGS. 2 and 3, whereas the containers are illustrated as being empty in FIG. 1.

Figure 3:
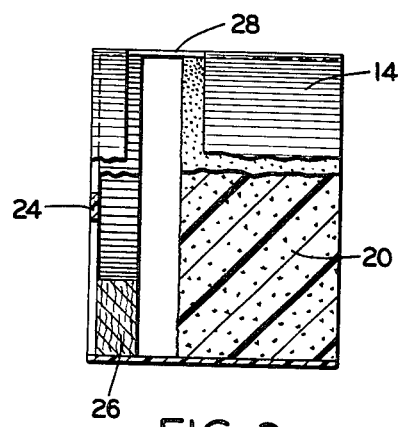
FIG. 3 is a cross sectional view of one of the containers shown in FIGS. 2 and 3 to expose the relative placement of the filter and medicament plug.
Figure 5:
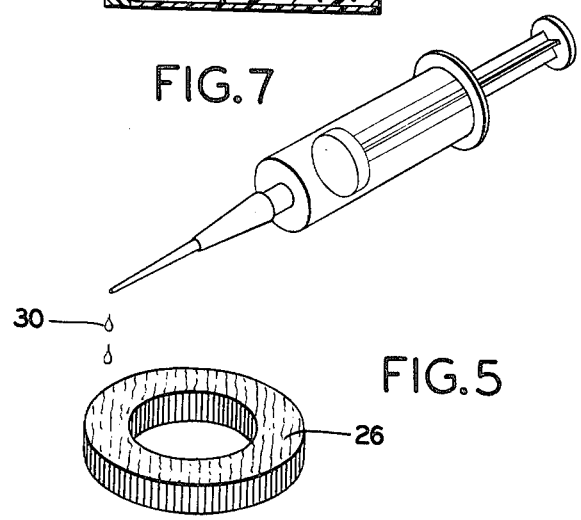
FIG. 5 is a perspective view of an absorbent, washer-shaped plug being saturated with a medicament.

Referring to FIGS. 3 and 5, the plug 26 is preferably in the form of an absorptive washer made of a porous material, such as cotton, wool, felt, paper or a synthetic foam, and is saturated with a medicament 30 to be inhaled through the nostrils. Alternatively, the plug 26 may be in the form of a washer-shaped solid which dispenses medication into the nasal air by sublimation. The provision of a washer-shaped plug in a nasal air filter and medicament dispenser unit is of particular significance; the central aperture 32 of the plug 26 does not impede air flow and exposes a maximum surface area of the medicament plug to air flow to be dispensed by evaporation or sublimation. This is of particular importance in a combination filter and medicament device since some resistance to breathing is necessarily caused by the filters 18 and 20; any additional substantial resistance to air flow by a conventional medicament plug having a uniform density would tend to be excessive. In addition, as nasal air flows through the central aperture of the plug 26, air turbulence created by contact with the inner surface wall of the plug increases evaporation or sublimation of the medicament (see FIG. 3).

Figure 7:
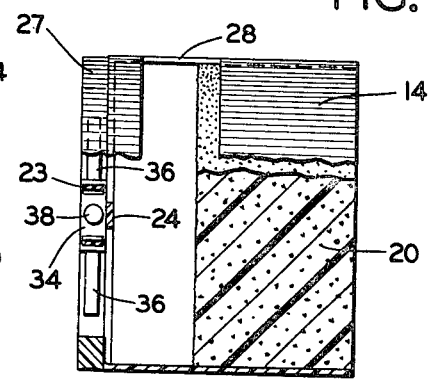
FIG. 7 is a cross sectional view of a nasal air filter in accordance with the invention including the sensor probes and dispensing nozzles shown in FIG. 6.
Figure 6:
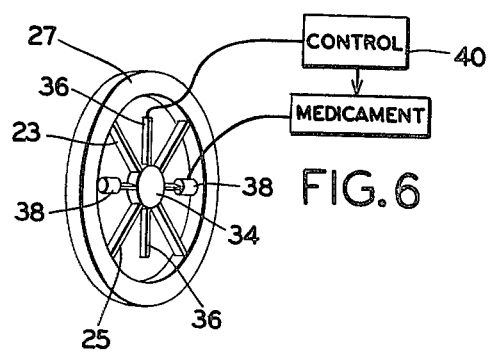
FIG. 6 is a perspective view of a portion of the nasal air filter and medicament dispensing device supporting a pair of optional sensor probes and dispensing nozzles.

Referring to FIG. 6, which discloses an optional probe and nozzle assembly identified generally by 27 bonded to one end of each container 12, 14 (FIG. 7), cross members 23 and 25 intersect a central mounting disc 34 supporting a pair of sensor probes 36 extending radially outwardly from the disc 34 as well as a pair of complementary dispensing nozzles 38. The purpose of sensors 36 is to monitor a parameter of air being inhaled through the nostrils for diagnostic purposes. For example, the probes may be responsive to the temperature of bacteriological content of the nasal air. Because the sensors 36 are positioned downstream of filters 18, 20 and medicament plug 26, as shown in FIG. 7, the air being sensed is the filtered and medicated air actually being inhaled. The purpose of nozzles 38 is to dispense an additional medicament in the form of a spray to be inhaled through the nostrils for therapeutic purposes. Other types of dispensers could be provided as elements 38, however. In addition, the elements 38 could, if desired, be provided as ionization probes to ionize air being inhaled as a therapeutic. The nozzles 38 may, in practice, be controlled by an external timer to dispense a charge of medicament into the nostrils at controlled intervals. The nozzles 38 may be controlled by the output of probes 36 through a conventional control circuit 40, as shown in FIG. 6.

In this disclosure, there is shown and described only the preferred embodiment of the invention, but as aforementioned, it is to be understood that the invention is capable of use in various other combinations and environments and is capable of changes or modifications within the scope of the inventive concept as expressed herein. For example, the assembly 27 carrying sensor probes 36 and nozzles 38 is optional, as indicated above, and may be omitted.

I claim:

1. A nasal insert comprising:
   a pair of dispenser devices adapted to be positioned within the nasal passages, each of said devices being formed of a resilient, cylindrical wall member;
   a connecting strip extending between said cylindrical members and adapted to bridge across the septum;
   an absorptive plug located within each of said cylindrical members and adapted to be saturated with a medicament;
   a sidewall of each of said cylindrical members being established by a continuous cylindrical surface, an access opening being formed in a portion of said surface for receiving said plug;
   a lower end of each of said cylindrical members including a filter element; and
   an upper end of each of said cylindrical members including a means for retaining said plug in said member while permitting axial air flow.

2. The insert of claim 1, wherein said absorptive plug is washer shaped to enable axial air flow through its central aperture.

3. The insert of claim 1, wherein said retaining means includes a pair of mutually orthogonal cross members extending radially within said cylindrical member.

4. The insert of claim 1, including a parameter probe means positioned within an air flow path in at least one of said cylindrical members, means for dispensing a medicament within said nasal passages and means responsive to said probe means for controlling said dispensing means.

5. The insert of claim 1, including means for storing a medicament; nozzle means adjacent said retaining means of at least one of said cylindrical members for dispensing medicament into an air flow path within said member; and means for controlling said nozzle means to dispense predetermined quantities of the medicament.

6. The insert of claim 1, wherein said approximately cylindrical members each has an elliptical radial cross section, the major and minor axes of said members corresponding to the configuration of the nasal passage.

7. A nasal insert comprising:
   a pair of dispenser devices adapted to be positioned with the nasal passages, each of said devices being formed of a resilient, cylindrical wall member;
   a connecting strip extending between said cylindrical members and adapted to bridge across the septum;
   a medicated plug located within each of said cylindrical members for dispensing a medication within said nasal passages;
   a sidewall of each of said cylindrical members being established by a continuous cylindrical surface, an access opening being formed in a portion of said surface for receiving said plug;
   a lower end of each of said cylindrical members including a filter element; and
   an upper end of each of said cylindrical members including means for retaining said plug in said member while permitting axial air flow.

8. The insert of claim 7, wherein said plug is washer shaped.

* * * * *